(12) United States Patent
Garthe et al.

(10) Patent No.: US 7,244,266 B2
(45) Date of Patent: Jul. 17, 2007

(54) SYSTEM FOR PAIN-REDUCED WITHDRAWAL OF BLOOD

(75) Inventors: Claus-Dieter Garthe, Lampertheim-Neuschloss (DE); Peter Ruschke, Budenheim (DE); Guenther Schmelzeisen-Redeker, Lorsch (DE); Claudio Immekus, Emmendingen (DE); Uschi Wolf, Darmstadt (DE); Klemens Masuch, Bergsteinfurt (DE); Hans List, Hesseneck-Kailbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 604 days.

(21) Appl. No.: 10/360,015

(22) Filed: Feb. 7, 2003

(65) Prior Publication Data

US 2003/0225429 A1    Dec. 4, 2003

(30) Foreign Application Priority Data

Feb. 15, 2002   (DE) ................. 102 06 254

(51) Int. Cl.
*A61B 17/14* (2006.01)
(52) U.S. Cl. ..................................... 606/181
(58) Field of Classification Search ................ 606/181, 606/183, 184, 185, 186, 187, 188
See application file for complete search history.

(56) References Cited

U.S. PATENT DOCUMENTS

| 4,014,347 | A | 3/1977 | Halleck et al. |
|---|---|---|---|
| 5,578,014 | A | 11/1996 | Erez et al. |
| 5,647,851 | A | 7/1997 | Pokras |
| 5,921,963 | A | 7/1999 | Erez et al. |
| 6,045,567 | A | 4/2000 | Taylor et al. |
| 6,210,420 | B1 * | 4/2001 | Mauze et al. ............... 606/182 |
| 6,231,531 | B1 | 5/2001 | Lum et al. |
| 6,306,152 | B1 | 10/2001 | Verdonk et al. |
| 2001/0027328 | A1 | 10/2001 | Lum et al. |

FOREIGN PATENT DOCUMENTS

| EP | 1074219 | 2/2001 |
|---|---|---|
| JP | 10-508527 | 8/1999 |
| JP | 11-164825 | 12/2000 |
| JP | 2001-87251 | 4/2001 |

(Continued)

OTHER PUBLICATIONS

Webster et al, "Use of Transcutaneous Electrical Nerve Stimulation for Fingertip Analgesia: A Pilot Study," Annals of Emergency Medicine, Jun. 29, 1992.
Wall, "The Gate Control Theory of Pain Mechanisms," Brain (1978), 101, 1-18.

(Continued)

*Primary Examiner*—Kevin T. Truong
(74) *Attorney, Agent, or Firm*—Woodard, Emhardt, Moriarty, McNett & Henry LLP

(57) ABSTRACT

Lancet system for pain-reduced blood withdrawal comprising an impulse generator which exerts an impulse on a body part in a sequence which is synchronized with the movement of a lancet. Method for the pain-reduced blood withdrawal in which an impulse is exerted on an adjacent body part in a sequence which is synchronized with the generation of an opening in the skin.

19 Claims, 5 Drawing Sheets

FOREIGN PATENT DOCUMENTS

Figure 1:
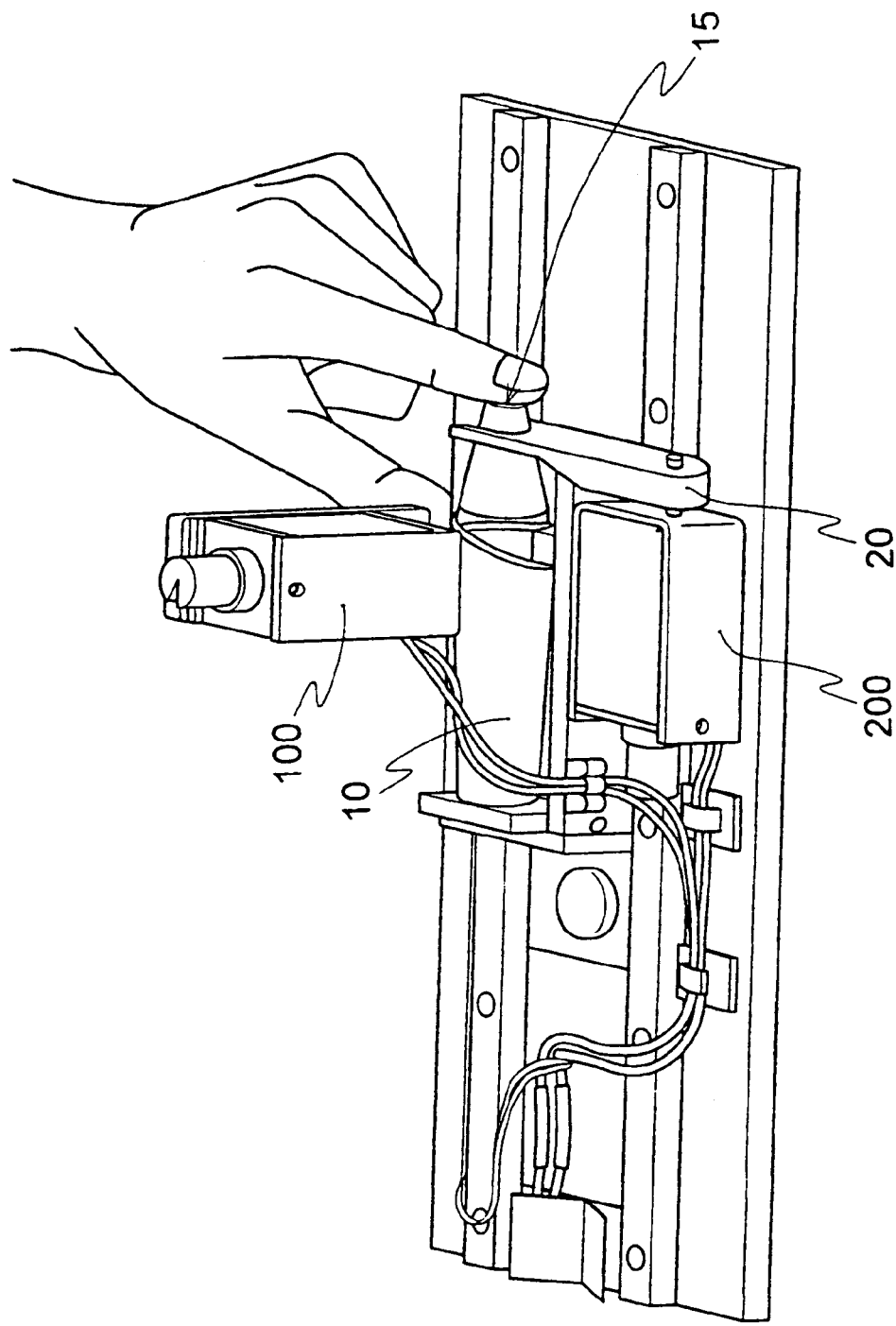

| | | |
|---|---|---|
| JP | 2000-237172 | 2/2002 |
| WO | WO 97/42885 | 11/1997 |
| WO | WO 97/4157 | 12/1997 |
| WO | WO 99/26539 | 6/1999 |
| WO | WO 01/62150 A1 | 8/2001 |

OTHER PUBLICATIONS

Melzack et al., "Pain Mechanisms: A New Theory," Science, vol. 150, No. 3699 (1965), pp. 971-979.

Wall et al., "Masking and Metacontrast Phenomena in the Skin Sensory System," Experimental Neurology 8, 35-46 (1963).

* cited by examiner

[FIG. 1]

Fig. 2
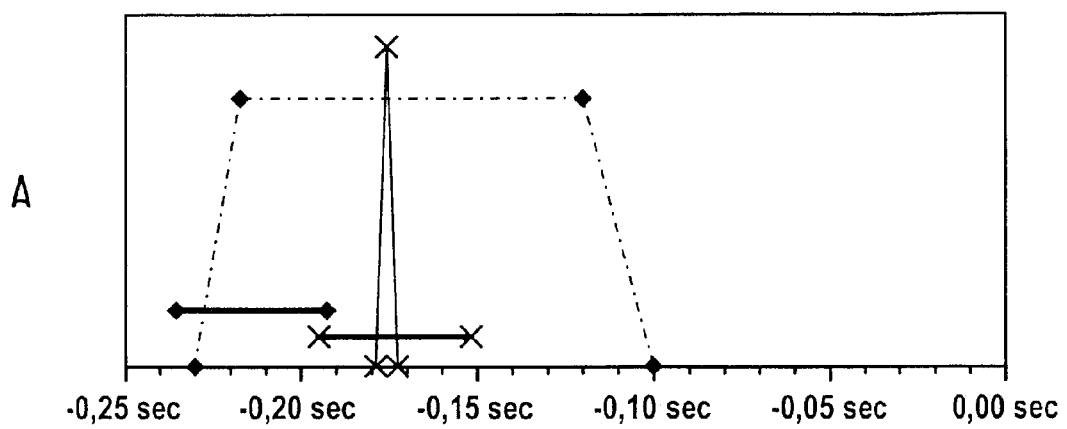
A
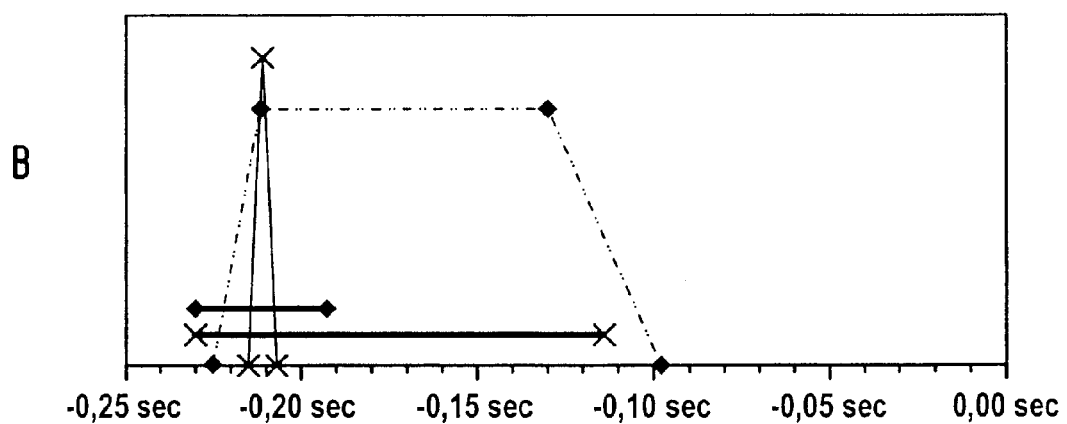
B
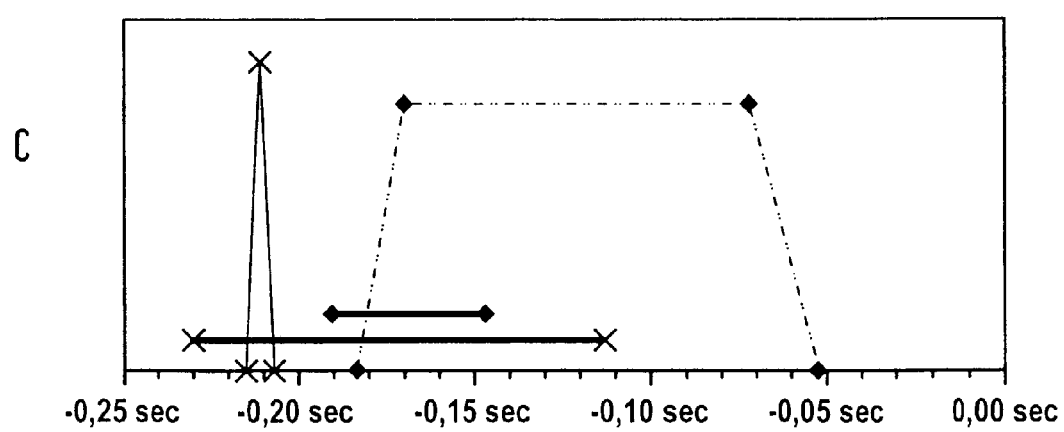
C

Fig. 3
I
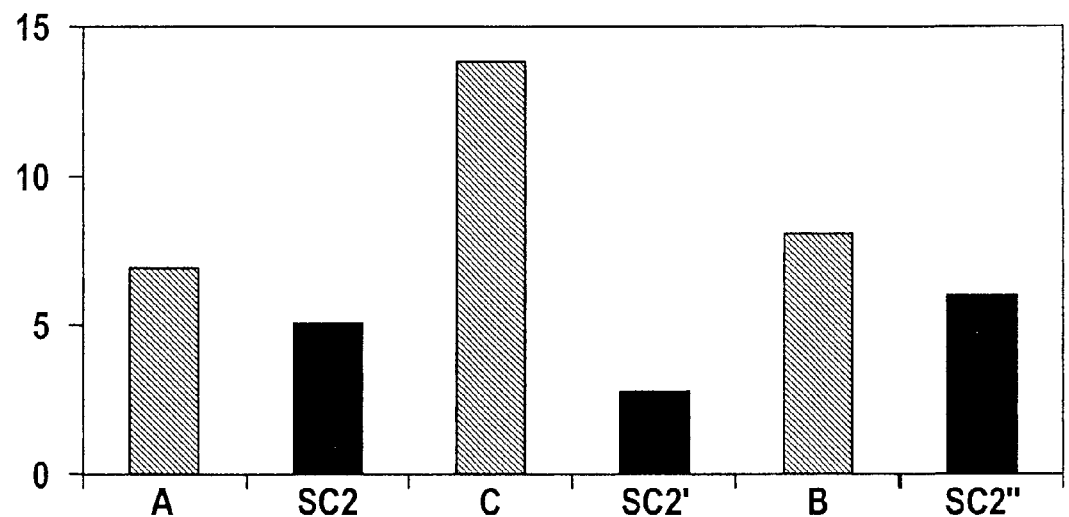
II
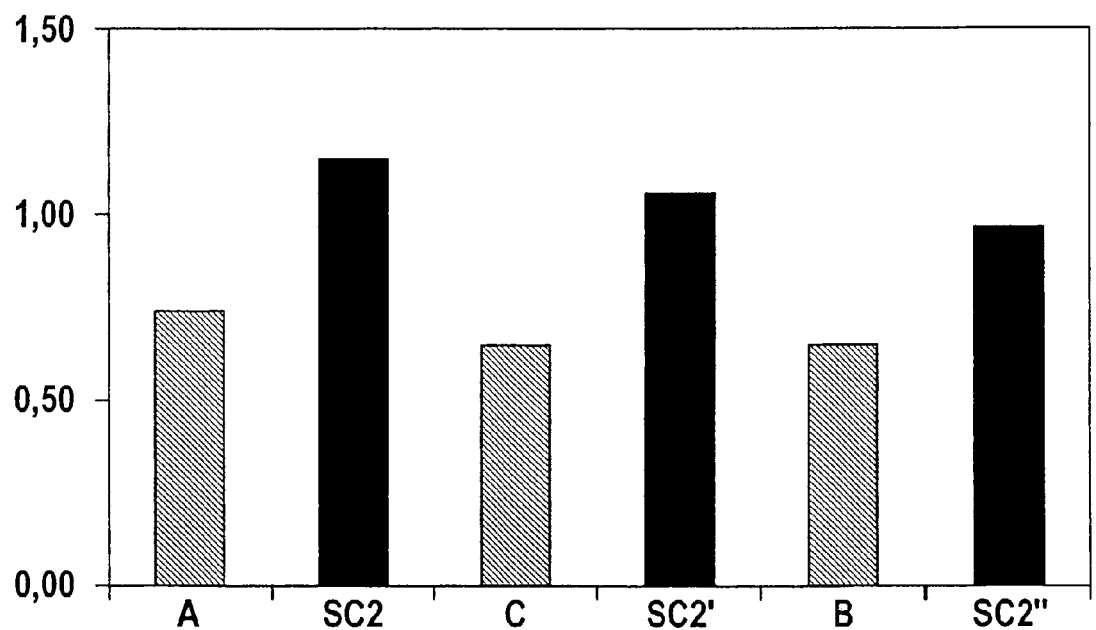

SYSTEM FOR PAIN-REDUCED WITHDRAWAL OF BLOOD

The present invention concerns a system for pain-reduced withdrawal of blood which comprises a lancet system which produces a small opening in the skin from which blood can emerge and an impulse generator which serves to reduce the pain sensation during blood withdrawal.

Systems for blood withdrawal are mainly used by diabetics to monitor the blood sugar level. However, such blood withdrawal devices are also used in doctor's offices, hospitals etc. if only small amounts of blood in the range of a few μl or less are required for an examination or analytical test. However, blood withdrawal devices have become particularly important for diabetics due to the necessity for frequent testing. In this case blood has to be constantly collected and often several times daily in order to avoid blood sugar values which are either too high or too low and thus reduce secondary damage. Whereas monitoring of the blood sugar level is virtually imperative for type I diabetics and is also carried out by the majority of the affected persons, many type II diabetics, the so-called maturity-onset diabetics, are much more careless about their disease and either do not carry out any blood sugar measurements or only irregularly. An important reason for this behaviour is the blood withdrawal required for analysis which is felt to be painful or at least unpleasant. Hence it is an important objective to substantially reduce the pain associated with blood withdrawal in order to make life easier for diabetics and also to motivate a larger number of type II diabetics to carry out blood sugar measurements. Hence the benefits would be both at a personal level as well as from an overall economic perspective by avoiding secondary damage.

Already several attempts have been made in the prior art to reduce the pain associated with the lancing. The shape of the lancet needle has a considerable effect on the pain that is caused and hence the pain can be reduced to a certain extent by optimizing the cut of the lancet needle. The lancing movement also has an influence on the pain level. In conventional systems in which the lancet is accelerated onto a stop by a spring, the needle vibrates during the piercing which causes pain. An improved blood lancet device is described in the European Patent 0 565 970 in which the lancet is continuously inserted and also removed from the wound by a drive which avoids an irregular vibrating movement of the needle tip.

A blood lancet device is described in WO 01/62150 which has hemispherical elevations on a cap that is pressed onto the skin for blood withdrawal which are intended to confuse the nerves which conduct the pain so that the puncture with the lancet is felt to be less painful by the user.

Figure 5:
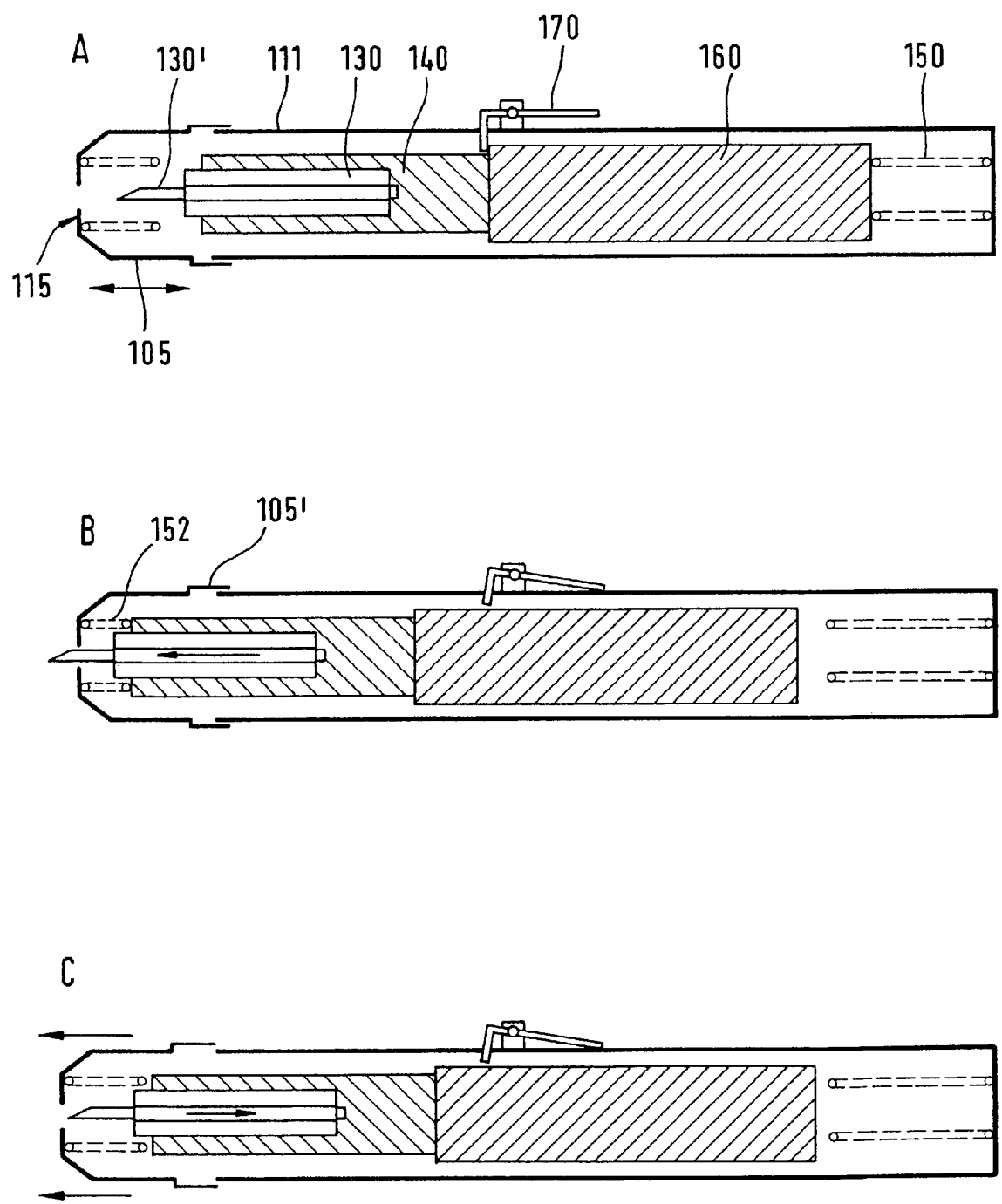

A lancet device is disclosed in U.S. Pat. No. 6,306,152 in which a weight and a lancet arranged in a hole through the weight are both accelerated by a spring. The weight and lancet both strike the body surface for blood withdrawal and the lancet moves further within the barrel due to its mass inertia so that it punctures the underlying tissue. The patent document describes that the barrel stretches the skin which stabilizes the skin and thus makes the puncture less painful. This is achieved in that the barrel restricts the freedom of movement of the skin in the area of the lancing site. However, the described device has a number of significant disadvantages for its practical application. As shown in FIG. 5 of U.S. Pat. No. 6,306,152 the maximum puncture depth of the lancet is determined by the length of a hole in the barrel in which the upper part of the needle moves. Since the puncture depth is predetermined by the length of the hole, it is not possible for the user to adjust the puncture depth in order to select a favourable puncture depth for his specific skin characteristics with which an adequate amount of blood can still be obtained for analysis with a minimum of pain. The movement of the lancet relative to the barrel by means of pure mass inertia causes other serious problems. On the one hand, with a given arrangement the available puncture depth may not be completely utilized since the acceleration is insufficient for skin penetration. This is exacerbated by the fact that in the manufacturing process it is technically difficult to adequately control the friction between the lancet and the barrel. In the worst case the lancet may jam due to manufacturing variations or even if the lancet is slightly bent so that mass inertia is not even sufficient for skin puncture. Another disadvantage is that in order to replace the lancet, which should occur after every skin puncture for reasons of hygiene, it is necessary to dismantle the barrel and remove the lancet from it or to replace the entire unit of barrel and lancet.

The object of the present invention was to propose a lancet device for blood withdrawal which minimizes the pain associated with withdrawal and enables a hygienic use.

This object is achieved by a lancet system for pain-reduced blood withdrawal which has a housing with a contact surface from which the tip of the lancet can emerge wherein the lancet located in a lancet holder is moved by means of a lancet drive and an impulse generator exerts an impulse on a part of the body which is synchronized with the lancing in order to reduce the pain sensation caused by the puncture.

The invention also proposes a method for pain-reduced blood withdrawal in which an impulse is exerted on a part of the body that is synchronized with the puncturing of a body surface.

The system and method according to the invention results in substantial improvements towards the goal of reducing the pain sensation associated with lancing. The puncture depth can be controlled and, if necessary, also regulated by the movement of the lancet holder and thus also of the lancet along a predetermined lancing path. Furthermore synchronization of the impulse exerted on the skin relative to the time of the puncturing of the body optimizes the effect of masking the pain.

The lancet system comprises a housing with a contact surface which a user of the system can position on a site on the body from which blood is to be withdrawn. The housing enables the user to handle the system and also protects the mechanism and the lancet from the environment. The contact surface which is pressed against the body has an opening through which the tip of a lancet can emerge from the interior of the housing in order to penetrate into the skin. The opening in the contact surface preferably has a cross-section of less than 5 mm and preferably between 1 and 3 mm. The contact surface which is pressed against the body for blood withdrawal can for example have the shape of a flat circular ring. However, it has proven to be advantageous for blood withdrawal from the finger pad to provide a small bulge on the contact surface in the direct vicinity of the exit opening which is for example in the shape of a ring around the exit opening in order to prestretch the skin in the lancing area. Furthermore protrusions can also be provided on the contact surface which protrude beyond the plane of the contact surface and thus stimulate the nerves when it is pressed against the body. A suitable arrangement is described in WO 01/62150. The contact surface can also have a contour or curvature to facilitate the escape of body fluid from the generated body opening. Such a contact surface which is also referred to as a stimulator surface is described in WO 99/26539. The contact surface may also be deformable in order to facilitate the withdrawal of body fluid in such a manner that a lateral movement occurs when the contact surface is pressed against the body surface which has a milking effect. Such a contact surface is described in the International Application WO 01/89383 to which reference is herewith made.

In the field of blood withdrawal systems replaceable lancets are commonly used which the user can replace for hygienic reasons after being used once or, under certain circumstances, several times. It is important that the lancets can be easily replaced especially when the blood withdrawal system is used by several persons. In conventional systems they are for example replaced by removing a cap at the front end of the housing and ejecting the lancet from a holder. However, it is also possible for the system to have a magazine for lancets into which a used lancet is retracted and/or a new lancet is inserted in the lancet holder.

A lancet is understood within the scope of this invention as a device which comprises a needle with a tip which is suitable for producing an opening in the body. Such a needle can for example be a solid needle as well as a hollow needle. Suitable materials for the needle are in particular metals and in particular high-quality steels and also blades made of flat steel, silicon, ceramics etc. Such a needle can be easily held in a holder of the blood withdrawal system. However, the lancet advantageously has a holding body in which the needle is located, in addition to the needle. Such holding bodies can be manufactured from plastic which is injected around the needle in an injection moulding process. This holding body enables the lancet to be held in a holder of the system. In addition the holding body can be designed such that it also encloses the tip region of the needle and thus protects it from contamination before use. Such a seal can be removed by unscrewing at a predetermined breaking point to expose the needle tip for blood collection. Since designs for holding a needle in a body and also for hygienically sealing the needle tip are well-known in the prior art, they are not described in more detail here.

The blood withdrawal system has a movable lancet holder to hold the lancet which can be moved along a predetermined path in order to carry out a puncture for blood collection. The lancet can for example be held in the lancet holder by pressure fitting or by wedging or locking. A particularly suitable lancet holder for the present invention is described in EP 0 565 970. However, the lancet holder does not necessarily have to be a body which encloses the lancet in a holding area, but it can for example also be a type of spike which is mounted on the lancet. Suitable combinations of lancets and lancet holders which enable a form-fitting coupling are described in PCT/EP01/12527. Such coupling methods are particularly favourable within the scope of the present application since the form-fitting connection enables a guided forwards movement of the lancet for puncturing as well as when it is retracted into the housing which has proven to be less painful.

The lancet holder is moved along a predetermined path by a lancet drive such that a lancet which is arranged in the lancet holder temporarily emerges from the exit opening and can pierce a body region which is located there. Numerous lancet drives are known from the prior art. There are drives in which a drive spring propels the lancet holder together with the lancet on to a stop and the body is punctured in the last part of this movement. The spring can be designed such that it retracts the lancet from the lancing position and adopts a resting position in which the needle is located within the housing. However, a second spring may also be provided to retract the needle into the housing which drives the lancet back from the lancing position into the housing. Positively guided systems may also be used as a drive such as crankshaft drives, lever drives or cam controls in which the movement of the lancet is not left to the free play of spring and mass forces but can be exactly predetermined by the drive mechanism. A drive according to EP 0 565 970 has proven to be particularly advantageous within the scope of the present invention in which the lancet holder is moved by a rotary slide gear. For this purpose the lancet drive has a sleeve with a groove in which a control pin moves which is connected to the lancet holder. When the sleeve is rotated about an axis parallel to the lancing direction, the pin moves within the groove and the movement of the lancet in the axial direction can be exactly predetermined within the tolerances by means of the shape of the groove. The guidance of the pin in the groove enables an exact mechanical guidance of the lancet in a positive as well as in a negative lancing direction during the movement. This guiding which is referred to as positive drive coupling enables the generation of defined paths and times for the lancing movement which have proven to be particularly painless.

A special feature of the blood withdrawal system according to the invention is an impulse generator which exerts an impulse on a body part which is synchronized with the piercing of the lancet. Such an impulse stimulates mechanoreceptors in the tissue. These receptors are connected to thick nerve fibres which have a high rate of conduction. In contrast pain receptors (nociceptors) that are activated by the puncturing are connected to thinner nerve fibres which conduct more slowly. The bone marrow represents a gate where the fibres arrive from the periphery and are connected. The thin nerve fibres from the nociceptors open the gate so that pain sensation can reach the brain. In contrast the thick nerve fibres of the mechanoreceptors close the gate. The balance between the signals arriving from the thin and thick fibres determines the pain sensation. These effects are also known under the term gate control theory.

A mechanical impulse which is exerted in synchronization with the piercing of the lancet can reduce or even completely suppress the pain sensation due to the needle puncture by exciting the mechanoreceptors. Since the signals of the mechanoreceptors are conducted more rapidly via the thick nerve fibres than the signals of the nociceptors, they are able to overtake the signals of the nociceptors even when the nociceptors are stimulated later and thus close the gate before the pain signal reaches it. Hence according to the invention the impulse can be exerted on the body region before the lancing as well as even shortly thereafter. Our investigations have shown that the impulse leads to a reduction of the perceived pain when it is triggered between 1000 and 0 milliseconds before the prick or between 0 and 100 milliseconds or preferably between 20 and 50 milliseconds after the prick.

The impulse on the body region can be exerted by the impulse generator via the contact surface of the housing or by a separate ram. The impulse generator and lancet drive can for example be constructed separately from one another and be controlled electrically by a control device. However, it has proven to be advantageous to mechanically couple the impulse generator and lancet drive such that the impulse and the lancing are coordinated by this mechanical coupling. Special embodiments of mechanical coupling are described in more detail in conjunction with the figures.

Blood withdrawal systems are usually relatively small devices for example in the form of a pen which is held manually. In such a device the impulse is generated by a relative movement of masses of a limited size. The ratio of the masses and their relative speed determines the force exerted on the body part which stimulates the receptors. It has proven to be advantageous to provide a mass for generating the impulse in the interior of the housing which is moved relative to the housing. If this mass is accelerated away from the contact surface by a drive, the housing and the contact surface exerts an impulse on the body part. In the case of an impulse transferred to the body by means of a ram, there is also a relative movement of masses in which the housing moves away from the body part.

It was found according to the invention that the impulse should preferably have a duration in the range of 0 to 10 or even better in the range of 1 to 7 milliseconds in order to achieve an efficient masking of the pain. This means that the impulse is not continuous but is cancelled again after a short time preferably by the blood withdrawal system itself by pulling the masses that have moved apart together again.

The force which is exerted by the impulse generator on the body part is preferably in the range of 10 to 30 N.

The invention is now elucidated in more detail on the basis of several examples:

FIG. 1: Blood withdrawal system with a ram as an impulse generator.

FIG. 2: Distance-time courses of the lancing and impulse using the system shown in FIG. 1.

FIG. 3: Assessment of the pain sensation by test persons with the distance-time courses shown in FIG. 2.

Figure 4:
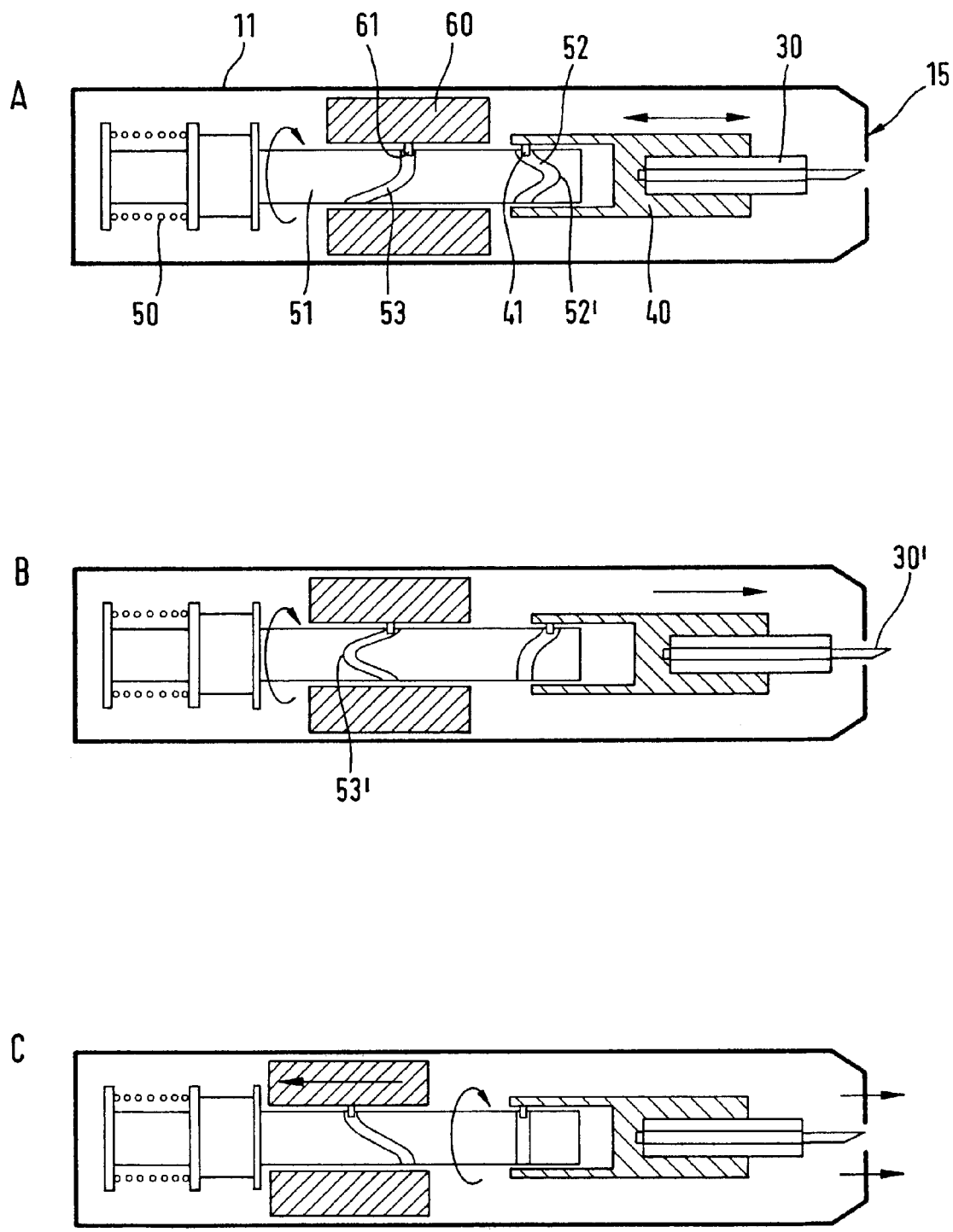

FIG. 4: Blood withdrawal system with a rotary slide gear.

FIG. 5: Blood withdrawal system with a spring-driven mass.

FIG. 1 shows a test construction for a blood withdrawal system with an impulse generator. The system comprises a conventional blood withdrawal system (10) as described in EP 0 565 970 which is commercially available under the name Softclix®. As shown the user presses his finger tip against the contact surface (15) from which a lancet needle emerges during the piercing process. The blood withdrawal system has an activating button that can be triggered by an electromechanical actuator (100). A ram (20) is located in the area of the contact surface that can be moved by a second electromechanical actuator (200) towards the body part. The first and second actuator are connected by an electrical control unit (not shown) which activates the actuators in a synchronized sequence. Various sequences of lancing using the blood withdrawal system and a slap with the fork (20) were examined with the arrangement shown in FIG. 1.

The time sequences are shown in FIG. 2. The curves indicated by the dashed line show the distance travelled by the fork (20) versus time. The thin continuous line shows the movement of the lancet over time. The thick horizontal lines indicate the time periods in which the actuators (100, 200) are triggered. The first actuator (100) which triggers the blood lancet has crosses at its ends whereas the activation phase of the second actuator (200) for the fork is shown by rhombi. FIG. 2A shows a situation in which an impact is triggered with the fork and the lancing is carried out while the fork is in the impact position. According to FIG. 2B the lancing was carried out while the fork begins its impact. In contrast FIG. 2C shows a situation in which the lancing occurs first and the impact begins about 0.03 sec later.

FIG. 3 shows an investigation on the pain sensation associated with the various time sequences. The experiments were carried out with 27 test persons and compared with corresponding blood withdrawals from the same test persons using a Softclix®. FIG. 3I shows the number of blood withdrawals which were felt to be painless by the test persons. The dashed bars correspond to the time sequences A, B, C shown in FIG. 2. The black bars directly adjoining the right hand side of each show the number of blood withdrawals that were felt to be painless using a conventional Softclix®. The figure shows that the number of blood withdrawals that were felt to be painless can be increased by exerting the impulse. In particular variant C in which the impact occurred ca. 30 msec after the puncture is favourable with regard to pain sensation.

FIG. 3II shows a ranking of the painfulness of the blood withdrawals with and without the slap. The hatched bars show averaged pain rankings that were obtained for the corresponding time sequences A, B, C from FIG. 2. The black bars to the right show reference measurements with the conventional Softclix®. This figure also shows that the pain sensation was considerably reduced on average by using the impulse.

FIG. 4 shows a path controlled system with a rotary slide gear which is based on the drive concept of EP 0 565 970. The system has a housing (11) for the manual handling and in which the drive mechanism is located. The drive comprises an elastic drive element, in the present case a spring (50), one end of which is attached to the housing and the other end is connected to a gear member which in this case is a guide sleeve (51). The spring (50) can be tensioned by turning the guide sleeve (51) such that it rotates in the direction shown in FIG. 4A when the spring relaxes. The sleeve (51) has two grooves (52, 53) of which the first (42) is used to drive the lancet holder (40). The sequence A, B, C shows how the lancet holder and thus the lancet (30) which is attached therein is moved when the sleeve (51) rotates. For this purpose the lancet holder (40) has a pin (41) attached thereto which moves within the first groove (52). The lancet holder is secured against rotation such that it is pushed forwards by the pin when the sleeve rotates from position A to position B and reaches the extreme point (52'). In this process the needle (30') of the lancet (30) emerges from the housing through an opening in the contact surface (15) and can puncture a body part that may be pressed against it. During this movement of the sleeve (51) which is approximately 45°, the pin (61) which is connected to a cylindrical mass (60) as an impulse weight is moved through an essentially straight region in the second groove (53). This means that while the sleeve is rotated from FIG. 4A to 4B, the mass (60) is only slightly accelerated. In the subsequent rotation from figure B to figure C the lancet holder is moved back such that the lancet tip moves into the housing. During this retraction the mass is subjected to a sharp change in its speed of movement with regard to quantity and/or direction when the pin (60) reaches its impact position (53'). This relative acceleration of the mass (60) and relative to the mass which is defined by the other system components, exerts an impulse on the housing in the direction of the contact surface such that it exerts an impact on a body part located on the contact surface. As a result of this mechanism of action it is apparent that the time interval between the lancing and the impact can be adjusted by means of the radial position of the extreme points (52') and (53') and by the speed of rotation of the sleeve (51). The grooves (52, 53) which act as control curves enable an exact predetermination of the distance-time course of the lancing and of the return movement as well as of the time course of the impact/impulse.

In this system it is advantageous when the mass of the drive mechanism and of the housing are relatively small but the mass of the impulse weight should be as large as possible such that the inner force which accelerates the two masses relative to one another results in the largest possible acceleration of the instrument housing. If the impulse weight were small in comparison to the mass of the housing and drive, this relative acceleration would be small.

FIG. 5 shows a blood withdrawal system with an impulse generator which comprises a drive with two elastic drive elements. A unit comprising a lancet holder (140) and a mass (160) attached thereto, the impulse mass, is located in the housing (111). This unit is tensioned against a drive spring (150) and locked with the lever (170). A lancet (130) with a needle (130') for producing an opening in the skin is located within the lancet holder. When the locking device (170) is released, the unit of lancet holder and mass and thus also the lancet is accelerated by the drive spring (150) towards the cap (105) on which the contact surface (115) is located. This forwards acceleration preferably occurs over a relatively long path in order to reduce the magnitude of the acceleration in this phase. In the end position shown in FIG. 5B, the needle (130') emerges from an opening in the contact surface (115) such that it can produce a skin opening in a body part pressed against the contact surface. FIG. 5B also shows that a second spring, the return spring (152), is pressed together starting from its resting position in FIG. 5A by the unit of lancet holder and mass. The forwards movement of the lancet holder and its mass are brought to a standstill by this spring and additionally by a solid stop in the cap in a preferred embodiment. This braking process occurs over a relatively short path which results in an acceleration of a large magnitude. Subsequently the lancet holder is retracted by the return spring and thus the needle is removed from the wound. The housing (111) and cap (105) are movably arranged axially to one another in that the cap (105) has a region with an enlarged inner cross-section (105') in which the front part of the housing (111) is inserted. This movability of the cap transfers the reaction force of the deceleration onto the cap which exerts an impact on a body part located at the contact surface. Alternatively the cap can be rigidly connected to the instrument housing. However, the movability of the cap enables the mass of the instrument housing to be used to capture the initial acceleration, but does not interfere with the transfer of the deceleration onto the cap by the moved mass and thus onto the body.

As already mentioned for the path-controlled drive according to FIG. 4, inner movements of mass have a greater outwards effect, the larger the impulse mass and the smaller the mass of the remaining instrument. In contrast in the case of the spring mass drive according to FIG. 5, it is advantageous when the mass of the housing is relatively large. When the lancing is triggered the impulse mass is accelerated forwards together with the lancet holder. In order to prevent this drive acceleration from lifting the instrument from the surface to be pierced, the reaction which is felt on the outside should be sufficiently small. This is achieved by long acceleration paths and thus small magnitudes of acceleration and/or by a large housing mass. In contrast at the time when the impact is exerted the deceleration of the lancet holder and its impulse mass should be transferred to the surface to be pierced with as little damping as possible which requires a housing mass which is small relative to the impulse mass. The movability of the cap then decouples a (small) part from the remaining housing on which the deceleration of the impulse mass acts and in this manner the two opposing objectives (no lifting from the body surface, strongest possible impulse on the body surface) can be achieved in a single instrument.

A mechanism is preferably used to tension the arrangement in which the cap is also returned to the initial position according to FIG. 5A when the lancet holder is retracted into the tensioned position according to FIG. 5A such that it again has the potential to move towards the contact surface when it is triggered.

In the system of FIG. 5 means can also be integrated to regulate the puncture depth. This can for example be achieved by a two part cap (105) which has a first part which consists of a region with an enlarged inner cross-section (105') and a thread. A second part consists of the pressure surface (115) and also has a thread which fits the first thread. The two parts are now screwed onto one another and the puncture depth can be regulated by screwing the parts together. In order to achieve a constant puncture depth it is also preferable to predefine the initial position shown in FIG. 5A in which the region having the widened inner cross-section is substantially filled by the housing (111) by a stop or other means.

The invention claimed is:

1. Lancet system for pain-reduced blood withdrawal comprising:
   a housing with a contact surface which has an exit opening for the tip of a lancet;
   a lancet holder for holding the lancet which can move in the housing along a lancing path;
   a lancet drive for moving the lancet holder along the lancing path; and
   an impulse generator which exerts an impulse on a body part in a sequence that is synchronized with the movement of the lancet holder so that a pain of piercing the skin can be reduced or even completely suppressed.

2. System as claimed in claim 1 which is designed such that the impulse is exerted between 0 and 100 ms after the tip of the lancet emerges from the exit opening.

3. System as claimed in claim 1 which is designed such that the impulse is exerted between 1000 and 0 ms before the tip of the lancet emerges from the exit opening.

4. System as claimed in claim 1 which has a device for adjusting the length of the lancet tip which protrudes beyond the contact surface.

5. System as claimed in claim 1 in which the impulse is transferred to the body via the contact surface.

6. System as claimed in claim 1 which has a rain for transferring the impulse to the body.

7. System as claimed in claim 1 in which the impulse generator and the lancet drive are mechanically coupled together.

8. System as claimed in claim 1 in which the impulse generator comprises a rotary slide gear which has an axis of rotation which is parallel to the lancing pat and which is driven by an Mastic drive element, and the system additionally comprises a mass whose movement is controlled by the gear member.

9. System as claimed in claim 8 in which the gear member controls the movement of the lancet holder.

10. System as claimed in claim 1 which has a cap that can be moved relative to the housing and on which cap the contact surface with the exit opening is located.

11. System as claimed in claim 10 which has an elastic drive element for moving the lancet holder into a lancing position and a second elastic drive element for retracting the lancet tip into the housing, wherein the second elastic drive element is mounted against the movable cap.

12. System as claimed in claim 1 in which the impulse generator exerts a maximum force in the range of 10 to 30 N on the body part.

13. System as claimed in claim 5 in which the contact surface or the ram has a profiled surface with which the impulse is applied.

14. Method for pain-reduced blood withdrawal comprising the steps:
- contacting a body part with a contact surface of a housing which has an exit opening for the tip of a lancet;
- moving a lancet holder with a lancer in the housing along a lancing path such that the tip of the lancet emerges through the exit opening beyond the contact surface; and
- exerting an impulse on a body part using an impulse generator which exerts an impulse on a body part in a sequence that is synchronized with the movement of the lancet holder so that a pain of piercing the skin can be reduced or even completely suppressed.

15. Method as claimed in claim 14 in which the impulse is exerted between 1000 and 0 ms before the tip emerges from the exit opening.

16. Method as claimed in claim 14 in which the impulse is exerted between 0 and 100 ms after the tip emerges from the exit opening.

17. Method as claimed in claim 14 in which the impulse has a duration in the range of 0 to 10 ms, preferably between 1 and 7 ms.

18. System as claimed in claim 1 which is designed such that the impulse is exerted between 20 and 50 ms after the tip of the lancet emerges from the exit opening.

19. Method as claimed in claim 14 in which the impulse is exerted between 20 and 50 ms after the tip emerges from the exit opening.

* * * * *

UNITED STATES PATENT AND TRADEMARK OFFICE
CERTIFICATE OF CORRECTION

PATENT NO.      : 7,244,266 B2                                          Page 1 of 1
APPLICATION NO. : 10/360015
DATED           : July 17, 2007
INVENTOR(S)     : Garthe et al.

It is certified that error appears in the above-identified patent and that said Letters Patent is hereby corrected as shown below:

In column 8, line 43, please change "rain" to --ram--.

In column 8, line 50, please change "pat" to --path--.

In column 8, line 51, please change "an Mastic" to --an elastic--.

Signed and Sealed this

Twentieth Day of November, 2007

JON W. DUDAS
*Director of the United States Patent and Trademark Office*